United States Patent
Moriya

(10) Patent No.: US 9,078,836 B2
(45) Date of Patent: Jul. 14, 2015

(54) BLOCK TYPE-MODIFIED ORGANOPOLYSILOXANE, METHOD FOR USING THE ORGANOPOLYSILOXANE, COSMETIC, AND METHOD FOR PRODUCING THE ORGANOPOLYSILOXANE

(71) Applicant: SHIN-ETSU CHEMICAL CO., LTD., Tokyo (JP)

(72) Inventor: Hiroyuki Moriya, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 13/868,235

(22) Filed: Apr. 23, 2013

(65) Prior Publication Data
US 2013/0302263 A1    Nov. 14, 2013

(30) Foreign Application Priority Data
May 11, 2012 (JP) ................. 2012-109850

(51) Int. Cl.
| | |
|---|---|
| A61K 8/18 | (2006.01) |
| A61K 8/895 | (2006.01) |
| C08G 77/46 | (2006.01) |
| A61Q 1/06 | (2006.01) |
| A61Q 1/10 | (2006.01) |
| A61Q 5/00 | (2006.01) |
| A61Q 17/04 | (2006.01) |
| A61Q 19/00 | (2006.01) |
| C08G 77/14 | (2006.01) |
| C08L 83/04 | (2006.01) |
| C08G 77/12 | (2006.01) |

(52) U.S. Cl.
CPC . *A61K 8/895* (2013.01); *A61Q 1/06* (2013.01); *A61Q 1/10* (2013.01); *A61Q 5/00* (2013.01); *A61Q 17/04* (2013.01); *A61Q 19/00* (2013.01); *C08G 77/14* (2013.01); *C08G 77/46* (2013.01); *C08L 83/04* (2013.01); *C08G 77/12* (2013.01)

(58) Field of Classification Search
None
See application file for complete search history.

(56) References Cited

U.S. PATENT DOCUMENTS

| | | | | |
|---|---|---|---|---|
| 4,025,456 | A | * | 5/1977 | Litteral et al. ............. 516/13 |
| 4,631,208 | A | | 12/1986 | Westall |
| 5,472,686 | A | | 12/1995 | Tsubaki et al. |
| 5,660,819 | A | | 8/1997 | Tsubaki et al. |
| 6,033,545 | A | | 3/2000 | Kaylo et al. |
| 6,245,828 | B1 | * | 6/2001 | Weinmann et al. .......... 522/148 |
| 2005/0261133 | A1 | | 11/2005 | Nakanishi et al. |
| 2007/0086968 | A1 | | 4/2007 | Leatherman et al. |
| 2007/0087937 | A1 | | 4/2007 | Leatherman et al. |
| 2010/0004201 | A1 | | 1/2010 | Matsuo et al. |

FOREIGN PATENT DOCUMENTS

| | | |
|---|---|---|
| EP | 1213011 A1 * | 6/2002 |
| EP | 2022812 A1 * | 2/2009 |
| JP | A-61-123635 | 6/1986 |
| JP | A-62-195389 | 8/1987 |
| JP | A-4-211605 | 8/1992 |

(Continued)

OTHER PUBLICATIONS

Apr. 4, 2014 Extended European Search Report issued in European Patent Application No. 13002312.0.

(Continued)

*Primary Examiner* — Robert A Wax
*Assistant Examiner* — Olga V Tcherkasskaya
(74) *Attorney, Agent, or Firm* — Oliff PLC

(57) ABSTRACT

A block type organopolysiloxane is represented by the following average composition formula (1),

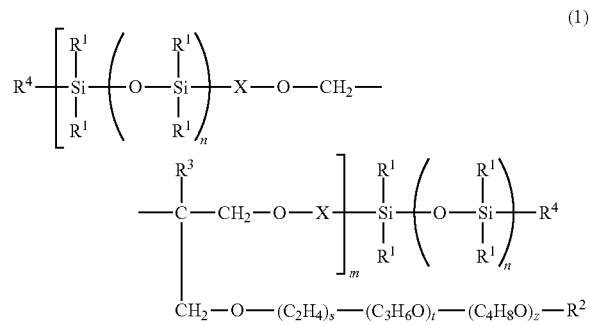

wherein each $R^1$ independently represents a monovalent hydrocarbon group having 1 to 12 carbons; $R^2$ represents any of a hydrogen atom, a monovalent hydrocarbon group having 1 to 15 carbons, and a monovalent acyl group having 2 to 7 carbons; $R^3$ represents a hydrogen atom or a monovalent hydrocarbon group having 1 to 4 carbons; X represents a divalent hydrocarbon groups having 2 to 15 carbons; "n" represents an integer of 1 or more; "m" represents an integer of 1 or more; "s" represents an integer of 0 to 100; "t" represents an integer of 0 to 50; "z" represents an integer of 0 to 50; each $R^4$ independently represents a hydrogen atom, a hydroxyl group, an alkoxy group, or an organic group represented by the general formula (2).

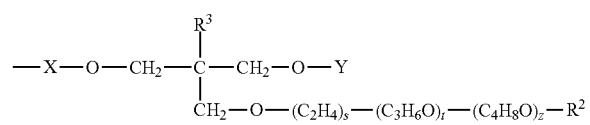

10 Claims, No Drawings

(56) References Cited

FOREIGN PATENT DOCUMENTS

| JP | A-4-234307 | 8/1992 |
| JP | A-5-163436 | 6/1993 |
| JP | A-2002-179797 | 6/2002 |
| JP | A-2005-344076 | 12/2005 |
| JP | A-2009-511710 | 3/2009 |
| JP | A-2009-511712 | 3/2009 |
| WO | WO 2009025924 A2 * | 2/2009 |

OTHER PUBLICATIONS

Mar. 31, 2015 Japan Patent Office Action issued in Japanese Application No. 2012-109850.

* cited by examiner

BLOCK TYPE-MODIFIED ORGANOPOLYSILOXANE, METHOD FOR USING THE ORGANOPOLYSILOXANE, COSMETIC, AND METHOD FOR PRODUCING THE ORGANOPOLYSILOXANE

BACKGROUND OF THE INVENTION

1. Field of the Invention

The present invention relates to a novel organopolysiloxane, a method for using the organopolysiloxane, a cosmetic containing the organopolysiloxane, and a method for producing the organopolysiloxane.

2. Description of the Related Art

A silicone oil has been conventionally blended into a cosmetic as an oil material to suppress stickiness and an oily feeling of the cosmetic. Meanwhile, the silicone oil is prone to many shortcomings such as undesirable fitting to the skin and insufficient moist feeling. To solve these problems, technical efforts have been made to provide an organopolysiloxane with improved surfactant property and sense of touch in use by introducing a polyether group into a dimethyl polysiloxane as a hydrophilic group (Japanese Unexamined Patent Publication No. S61-123635).

Nevertheless, despite easy design structure in this type of silicone, a silicone whose degree of polymerization is high may involve a residual unreacted polyether and thus a problematic surfactant performance, resulting in unstable cosmetic sustainability. Moreover, emulsion stability is achieved by introducing a silicone whose structure is branched, but unfortunately, a method for producing a silicone compound by introducing the branched structure is not fully simplified for production (Japanese Unexamined Patent Publication No. 2002-179797).

In addition, an (AB)n type organopolysiloxane copolymer in which a silicone unit and a polyoxyethylene unit are alternately bonded is proposed (Japanese Unexamined Patent Publication No. H4-21 1605: Japanese Unexamined Patent Publication No. H4-234307; Japanese Unexamined Patent Publication No. H 5-163436). This type of alternating copolymer is advantageous in the reduction in residual unreacted organopolysiloxane and unreacted polyether. However, a silicone having the linear repeating unit may provide senses of weight and stickiness for a cosmetic containing the same.

Another copolymer, such as an AB type or an ABA type organopolysiloxane copolymer, in which only 2 or 3 polyether units such as a silicone unit and a polyoxyethylene unit are bonded, is proposed. However, emulsion stability therein is insufficient as a surfactant (Japanese Unexamined Patent Publication No. 2005-344076; Japanese Unexamined Patent Publication No. S62-195389; Japanese Unexamined Patent Publication No. 2009-511710; Japanese Unexamined Patent Publication No. 2009-511712). Accordingly, production of an organopolysiloxane copolymer has conventionally required additional improvements to serve as a more useful surfactant and cosmetic ingredient.

SUMMARY OF THE INVENTION

The present invention was made to solve the problems mentioned above, and was intended to provide an organopolysiloxane that can provide a cosmetic excellent in cosmetic sustainability having excellent emulsion stability and temporal stability and thus light feeling and non-stickiness.

To solve the problems mentioned above, the present invention provides a block type organopolysiloxane represented by the following average composition formula (1),

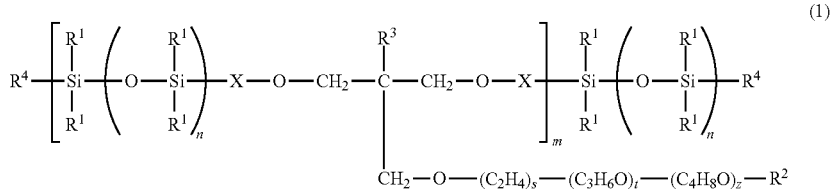

(1)

wherein each $R^1$ independently represents a monovalent hydrocarbon group having 1 to 12 carbons; $R^2$ represents any of a hydrogen atom, a monovalent hydrocarbon group having 1 to 5 carbons, and a monovalent acyl group having 2 to 7 carbons; $R^3$ represents a hydrogen atom, or a monovalent hydrocarbon group having 1 to 4 carbons; X represents a divalent hydrocarbon group having 2 to 5 carbons; "n" represents an integer of 1 or more; m represents an integer of 1 or more; "s" represents an integer of 0 to 100; "t" represents an integer of 0 to 50; z represents an integer of 0 to 50; and each $R^4$ independently represents a hydrogen atom, a hydroxyl group, an alkoxy group, or an organic group represented by the following general formula (2),

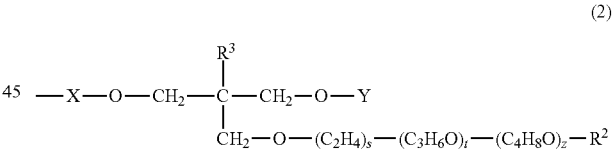

(2)

wherein X, $R^2$, $R^3$, "s", "t", and "z" are the same as above, and Y represents a hydrogen atom, or a monovalent hydrocarbon group having 2 to 5 carbons having a carbon-carbon double bond.

The block type organopolysiloxane having the specific structure is defined as a block structure composed of a polysiloxane moiety and a hydrophilic moiety, comprising a non-linear and pendant-type polyether chain of a hydrophilic group. By containing the same, the block type organopolysiloxane can provide a cosmetic excellent in cosmetic sustainability having excellent emulsion stability and temporal stability and thus light feeling and non-stickiness.

The block type organopolysiloxane is preferably a compound represented by the following average composition formula (3),

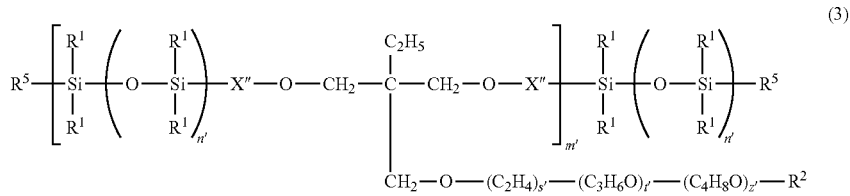

wherein each $R^1$ independently represents a monovalent hydrocarbon group having 1 to 12 carbons; $R^2$ represents any of a hydrogen atom, a monovalent hydrocarbon group having 1 to 5 carbons, and a monovalent acyl group having 2 to 7 carbons; X" represents —$(CH_2)_3$— or $CH_2CH(CH_3)CH_2$—; "n'" represents an integer of 1 to 2000; "m'" represents an integer of 1 to 1000; "s'" represents an integer of 1 to 100; "t'" represents an integer of 0 to 50; "z'" represents an integer of 0 to 50; each $R^5$ independently represents a hydrogen atom, a hydroxyl group, an alkoxy group having 1 to 6 carbons, or an organic group represented by the following general formula (4),

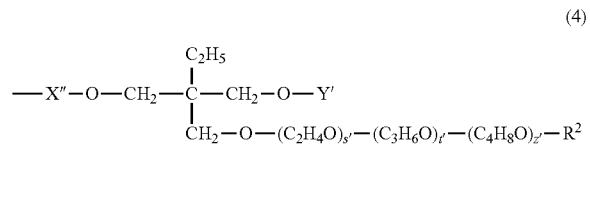

wherein X", $R^2$, "s'", "t'", and "z'" are the same as before, and Y' represents a hydrogen atom, —$CH_2$—$CH$=$CH_2$, —$CH$=$CH$—$CH_3$, —$CH_2$—$C(CH_3)$=$CH_2$, or —$CH$=$C(CH_3)_2$.

The block type organopolysiloxane is preferably a compound represented by the above average composition formula (3), and the block type organopolysiloxane having the specific structure can be readily produced and production costs can be reduced.

The present invention provides a cosmetic comprising the block type organopolysiloxane.

The cosmetic of the present invention is a cosmetic excellent in cosmetic sustainability having excellent emulsion stability and temporal stability and thus light feeling and non-stickiness by containing the above block type organopolysiloxane of the present invention.

The cosmetic further contains any of water, a silicone oil, an ester oil, and a glyceride oil, or a mixture thereof, and can be in the form of emulsion.

As mentioned above, the cosmetic of the present invention can be a cosmetic in any form, depending on the use thereof.

The present invention provides a method for using a block type organopolysiloxane, wherein the block type organopolysiloxane is used as a surfactant.

The block type organosiloxane of the present invention is excellent in emulsion stability and temporal stability as a surfactant, and can provide favorable emulsion stability and temporal stability for the cosmetic to which the organosiloxane is blended.

Moreover, the present invention provides a method for producing the block type organopolysiloxane, wherein a both-end hydrogen organopolysiloxane represented by the following general formula (5) and a compound represented by the following general formula (6) are reacted in the presence of a transition metal catalyst,

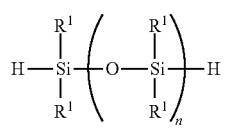

wherein $R^1$ and "n" are the same as before, $$[X'-O-CH_2\overline{)_2}C-CH_2-O-(C_2H_4O)_s-(C_3H_6O)_t-(C_4H_8O)_z-R^2$$
(6)

with $R^3$ on the central carbon wherein X' represents a monovalent hydrocarbon group having 2 to 5 carbons having a carbon-carbon double bond on its one end, and $R^2$, $R^3$, "s", "t", and "z" are the same as before.

The above production method can produce a block type organopolysiloxane under various conditions, with not particularly restricted reaction temperature and time of reaction.

In this case, a platinum or a rhodium can be used as the transition metal catalyst.

By using the above transition metal catalyst, polymerization reaction can be made at low temperature.

The block type organosiloxane of the present invention is excellent in emulsion stability and temporal stability, and can provide a cosmetic excellent in cosmetic sustainability.

DESCRIPTION OF THE PREFERRED EMBODIMENTS

The present invention will be described in more details.

A Novel Block Type Organopolysiloxane

The present invention provides a block type organopolysiloxane represented by the following average composition formula (1),

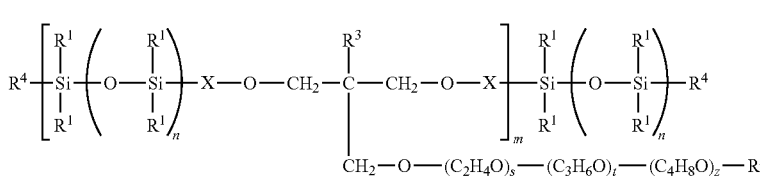

(1)

wherein each $R^1$ independently represents a monovalent hydrocarbon group having 1 to 12 carbons; $R^2$ represents any of a hydrogen atom, a monovalent hydrocarbon group having 1 to 15 carbons, and a monovalent acyl group having 2 to 7 carbons; $R^3$ represents a hydrogen atom or a monovalent hydrocarbon group having 1 to 4 carbons; X represents a divalent hydrocarbon groups having 2 to 15 carbons; "n" represents an integer of 1 or more; "m" represents an integer of 1 or more; "s" represents an integer of 0 to 100; "t" represents an integer of 0 to 50; "z" represents an integer of 0 to 50; and each $R^4$ independently represents a hydrogen atom, a hydroxyl group, an alkoxy group, or an organic group represented by the following general formula (2),

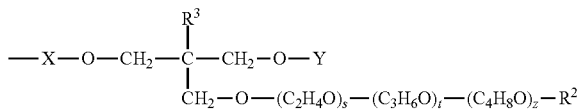

(2)

wherein X, $R^2$, $R^3$, "s", "t", and "z" are the same as before, and Y represents a hydrogen atom, or a monovalent hydrocarbon group having 2 to 15 carbons having a carbon-carbon double bond.

In the above average composition formula (1), illustrative example of the $R^1$ includes an alkyl group such as a methyl group, an ethyl group, a propyl group, a butyl group, a pentyl group, a hexyl group, a heptyl group, an octyl group, a nonyl group, and a decyl group; a cyclic alkyl group such as a cyclopentyl group and a cyclohexyl group; and an aryl group such as a phenyl group, a tolyl group, a benzyl group, and a phenethyl group, and preferably a methyl group and a phenyl group. It is preferable that 50% or more of $R^1$ contained in the organopolysiloxane molecule be a methyl group, or most preferably 70% or more of $R^1$ be a methyl group. Illustrative example of the $R^2$ includes a hydrogen atom; an alkyl group such as a methyl group, an ethyl group, a propyl group, a butyl group, a pentyl group, and a hexyl group; an aryl group such as a phenyl group; and an acyl group such as an acetyl group, a propionyl group, and a benzoyl group. Illustrative example of the $R^3$ includes a methyl group, an ethyl group, a propyl group, and a butyl group, and preferably an ethyl group.

Illustrative example of the $R^4$ includes a hydrogen atom; a hydroxyl group; an alkoxy group such as a methoxy group, an ethoxy group, an n-propoxy group, a butoxy group; and an organic group represented by the general formula (2), and preferably a hydrogen atom, a hydroxyl group, a methoxy group, an ethoxy group, a 1-propoxy group, a 2-propoxy group, and an organic group represented by the general formula (2). Illustrative example of the X includes a divalent hydrocarbon group having 2 to 15 carbons, and preferably such as $-(CH_2)_2-$, $-(CH_2)_3-$, $-(CH_2)_4-$, $-CH_2CH(CH_3)CH_2-$, $-(CH_2)_8-$, and $-(CH_2)_{11}-$, and more preferably $-(CH_2)_2-$, $-(CH_2)_3-$, and $-CH_2CH(CH_3)CH_2-$. "n" represents an integer of 1 or more, preferably 1 to 2000, and more preferably 5 to 100. "m" represents an integer of 1 or more, preferably 1 to 1000, more preferably 1 to 100, and much more preferably 3 to 20. "s" represents an integer of 0 to 100, preferably 1 to 50, and more preferably 5 to 50. "t" represents an integer of 0 to 50, and preferably 0 to 30. "z" represents an integer of 0 to 50, and preferably 0 to 20. A pendant-type alkyleneether moiety is a random or a block copolymer. In the formula (2), X, $R^2$, $R^3$, "s", "t", and "z" are the same as before, and Y represents a hydrogen atom, or a monovalent hydrocarbon group having 2 to 15 carbons having a carbon-carbon double bond, and preferably an ethylene group, a propylene group, a butylene group, a branched butylene group, an octene group, and a dodecen group.

The organopolysiloxane represented by the above average composition formula (1) is preferably, for example, the organopolysiloxane represented by the following average composition formula (3),

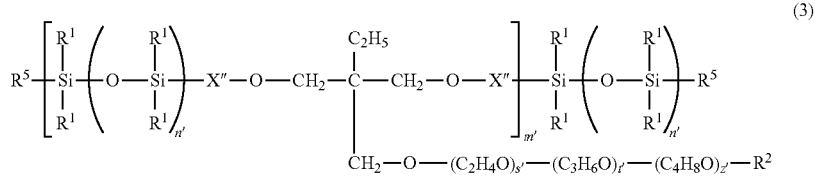

(3)

wherein each $R^1$ independently represents a monovalent hydrocarbon group having 1 to 12 carbons; $R^2$ represents any of a hydrogen atom, a monovalent hydrocarbon group having 1 to 15 carbons, and a monovalent acyl group having 2 to 7 carbons; X" represents $-(CH_2)_3-$ or $-CH_2CH(CH_3)CH_2-$; "n'" represents an integer of 1 to 2000; "m'" represents an integer of 1 to 1000; "s'" represents an integer of 1 to 100; "t'" represents an integer of 0 to 50; "z'" represents an integer of 0 to 50; and each $R^5$ independently represents a hydrogen atom, a hydroxyl group, an alkoxy group having 1 to 6 carbons, or an organic group represented by the following general formula (4), (4)

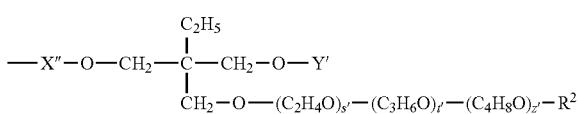

wherein X'', $R^2$, "s'", "t'", and "z" are the same as before, and Y' represents a hydrogen atom, $-CH_2-CH=CH_2$, $-CH=CH-CH_3$, $-CH_2-C(CH_3)=CH_2$, or $-CH=C(CH_3)_2$.

Illustrative example of the block type organopolysiloxane of the present invention will be described.

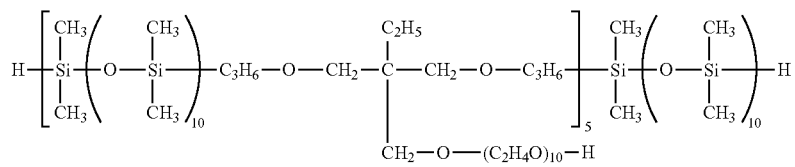

The above block type organopolysiloxane is defined as a both-end hydrogen atom type, and it can be obtain as an alkoxylated organopolysiloxane by dehydrogenation by using an alcohol as the later-mentioned reaction solvent. If water is contained in a reaction system, an organopolysiloxane obtained can be substituted with a hydroxyl group by dehydrogenation.

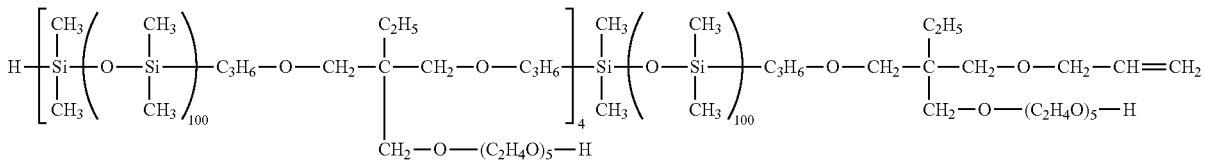

There exists a residual double bond in the above block type organopolysiloxane on its one end thereof, which can be internally transferred during a reaction.

Production Method

The present invention provides a method for producing the above-mentioned block type organopolysiloxane, comprising reacting a both-end hydrogen organopolysiloxane represented by the following general formula (5) and a compound represented by the following general formula (6) in the presence of a transition metal catalyst, (5)

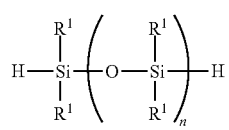

wherein $R^1$ and "n" are the same as before.

(6)

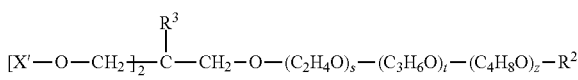

wherein X' represents a monovalent hydrocarbon group having 2 to 15 carbons having a carbon-carbon double bond on its one end, preferably $CH=CH-$, $CH=CH-CH_2-$, $CH=CH-(CH_2)_2-$, $CH=C(CH_3)CH_2-$, $CH=CH-(CH_2)_6-$, and $CH=CH-(CH_2)_9-$, and more preferably $CH=CH-CH_2-$, $CH=C(CH_3)CH_2-$. $R^2$, $R^3$, "s", "t", and "z" are the same as before.

Illustrative example of the method for producing the compound represented by the above general formula (6) includes the method by adding an ethylene oxide, a propylene oxide, and a butylene oxide alone or in combination therewith in the presence of a base or an acid catalyst by using a trimethylolpropane diallyl ether as a starting material. The method by an addition reaction of the above alkylene oxide with a hydroxy group is known. The degree of purity of the trimethylolpropane diallyl ether is preferably 50% or more, and more preferably 80% or more.

Illustrative example of the transition metal catalyst includes a platinum and a rhodium, and preferably a chloroplatinic acid, an alcohol-modified chloroplatinic acid, and a chloroplatinic acid-divinylsiloxane complex. Amount of the catalyst used may be allowable if it is usable as a catalyst, normally 50 ppm or less in terms of a platinum or a rhodium, and preferably 20 ppm or less.

The reaction temperature is not particularly restricted, but its boiling point or less if an organic solvent is used, and preferably in the range of 50° C. to 140° C. in a solvent-free reaction. If the reaction temperature is 140° C. or less, a carbon-carbon double bond on its one end of an organopolysiloxane is not internally transferred easily, thereby showing a favorable reactivity. The time of reaction is not particularly restricted, but preferably in the range of 1 to 10 hours.

This reaction may be carried out in an organic solvent as appropriate. Illustrative example of the organic solvent includes an aromatic hydrocarbon such as toluene and xylene; a lower alcohol such as ethanol and isopropyl alcohol; an aliphatic or an alicyclic hydrocarbon such as n-pentane, n-hexane, and cyclohexane; a halogen-containing hydrocarbon such as dichloromethane, chloroform, and carbon tetrachloride; and ether such as tetrahydrofurane and dioxane. Preferably, an aromatic, an aliphatic, an alicyclic hydrocarbon solvent, or a lower alcohol is used.

In the reaction, the compound represented by the general formula (6) is preferably 0.7 to 1.4, and more preferably 0.9 to 1.1, per equivalent of the organopolysiloxane represented by the general formula (5).

The block type organopolysiloxane of the present invention can be used for a personal care composition, a cosmetic, fiber treatment, a coating material, resin modification and so on.

Cosmetic

The present invention provides a cosmetic comprising the block type organopolysiloxane. The cosmetic of the present invention is excellent in cosmetic sustainability having excellent emulsion stability and temporal stability and thus light feeling and non-stickiness.

The present invention provides a cosmetic excellent particularly in cosmetic sustainability by containing 0.1 to 40% by mass of the organopolysiloxane, relative to the total amount of the cosmetic.

Other than the above organopolysiloxane, a solid, a semi-solid or a liquid oil material, water, an alcohol, a surfactant, a powder used in a normal cosmetic can be added to the cosmetic of the present invention. The present invention is not restricted thereto.

Illustrative example of the oil material that can be used in the present invention includes the following oils. Illustrative example of the natural vegetable and animal fatty oil and the semi-synthetic oil include an avocado oil, a linseed oil, an almond oil, a privet wax, a perilla oil, an olive oil, a cacao butter, a kapok wax, a kaya oil, a carnauba wax, a lever oil, a candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a rhea butter, a Chinese tung oil, a cinnamon oil, a jojoba wax, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse wax, a Persic oil, a palm oil, a palm kernel oil, a castor oil, a cured castor oil, a methyl ester of cured castor oil fatty acid, a sunflower oil, a grape seed oil, a bayberry wax, a jojoba oil, a macadamia nut oil, a bees wax, a mink oil, a cotton seed oil, a cotton wax, a Japan wax, a Japan wax kernel oil, a montan wax, a coconut oil, a cured coconut oil, a tri-coconut oil fatty acid glyceride, a mutton tallow, a peanut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. Meanwhile, POE means polyoxyethylene.

Illustrative example of the hydrocarbon oil includes an ozocerite, squalane, squalene, a ceresin, a paraffin, a paraffin wax, a liquid paraffin, a pristane, polyisobutylene, a microcrystalline wax, and vaseline. Illustrative example of the higher fatty acids includes lauric acid, myristic acid, palmitic acid, stearic acid, behenic acid, undecylenic acid, oleic acid, linoleic acid, linolenic acid, arachidonic acid, eicosapentaenoic acid, docosahexaenoic acid, isostearic acid, and 12-hydroxystearic acid.

Illustrative example of the higher alcohol includes lauryl alcohol, myristyl alcohol, palmityl alcohol, stearyl alcohol, behenyl alcohol, hexadecyl alcoho, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glyceryl ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, neopentylglycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, dextrin palmitic acid ester, dextrin stearic acid ester, dextrin 2-ethyl hexanoic acid palmitic acid ester, sucrose palmitic acid ester, sucrose stearic acid ester, monobenzylidene sorbitol, and dibenzylidene sorbitol.

Illustrative example of the glyceride oil includes acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

Illustrative example of the silicone oil includes dimethyl polysiloxane, methyl phenyl polysiloxane, methyl hydrogen polysiloxane, octamethyl ciclotetrasiloxane, decamethyl cyclopentasiloxane, dodecamethyl cyclohexasiloxane, tetramethyl tetrahydrogen ciclotetrasiloxane, and a silicone modified with a higher alkoxy such as stearoxysilicone, a higher fatty acid-modified silicone, a fluorine-modified silicone, an amino-modified silicone, an alkyl-modified silicone, a higher fatty acid ester-modified silicone, a silicone resin, and a silicone rubber, a di-silicone resin. Illustrative example of the fluorinated oil material includes perfluoro polyether, perfluoro decalin, and perfluoro octane.

One, or two or more kinds of these oil materials can be used as appropriate. Amount of these oil materials to be blended into the cosmetic of the present invention is in the range of 0 to 90% by mass, and particularly preferably 1 to 90% by mass.

Amount of water to be blended into the cosmetic of the present invention is in the range of 0 to 99.0% by mass.

The cosmetic of the present invention can be in the form of emulsion by containing any of a silicone oil, an ester oil, a glyceride oil, and water, or a mixture thereof.

Illustrative example of the alcohol that can be used in the present invention includes ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, polyglycerin, pentaerythritol, sucrose, lactose, xylitol, sorbitol, mannitol, maltitol, carrageenan, agar, guar gum, dextrin, tragacanth gum, locust bean gum, a polyvinyl alcohol, polyoxyethylene-based polymer, a polyoxyethylene/polyoxypropylene copolymer-based polymer, hyaluronic acid, chondroitin sulfate, and chitin chitosan, and one, or two or more kinds thereof can be used as appropriate. Amount of the alcohol to be blended into the cosmetic is in the range of 0.1 to 90.0% by mass, and preferably 0.5 to 50.0% by mass. The amount of the alcohol of 0.1% by mass or more is preferable due to sufficient moisture retention, antimicrobe and antibacterial properties.

The cosmetic of the present invention can be more excellent in property with an oil material, water, and an alcohol added thereto, but the following components i), ii), iii), and iv) can be further added thereto as appropriate.

i) Powder and/or Coloring Agent Shown Below

Illustrative example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montmorillonite, hectorite, zeolite, ceramics powder, dibasic calcium phosphate, alumina, aluminum hydroxide, boron nitride, and silica.

Illustrative example of the organic powder includes a polyamide powder, a polyester powder, a polyethylene powder, a polypropylene powder, a polystyrene powder, a polyurethane powder, a benzoguanamine powder, a polymethyl benzoguanamine powder, a tetrafluoroethylene powder, a polymethyl methacrylate powder, a cellulose powder, a silk powder, a nylon powder such as a 12 nylon powder and a 6 nylon powder, a styrene-acrylic acid copolymer, a divinyl benzene-styrene copolymer, a vinyl resin, a urea resin, a phenolic resin, a fluorinated resin, a silicone resin, an acryl resin, a melamine resin, an epoxy resin, a polycarbonate resin, a fine crystalline fiber powder, a starch powder, and lauroyl lysine.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as a yellow iron oxide and a yellow earth; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders.

Illustrative example of the pearl pigment includes a mica coated with titanium oxide, oxychloro bismuth, oxychloro bismuth coated with titanium oxide, a talc coated with titanium oxide, a fish scale foil, and a colored mica coated with titanium oxide. Illustrative example of the metal powder pigment includes an aluminum powder, a copper powder, and a stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Illustrative example of the natural dye includes carminic acid, laccaic acid, carthamin, brazilin, and crocin.

As to the powder like this, any powder may be used regardless of its form (spherical, needle-like, plate-like, and so on), its particle diameter (fumed, microparticle, pigment-class, and so on), and its particle structure (porous, non-porous, and so on), provided that the powder is used in a usual cosmetic. In addition, usable are powders obtained by hybridizing, or surface-treating these powders, with an oil material, a silicone other than the organopolysiloxane of the present invention, or a fluorine-containing compound, and the like.

ii) Surfactant Shown Below

Illustrative example of the anionic surfactant includes a saturated or an unsaturated fatty acid soap such as sodium stearate and triethanolamine oleate, an alkyl ether carboxylic acid and a salt thereof, a carboxylic acid salt such as a condensate between an amino acid and a fatty acid, an amide ether carboxylic acid salt, an α-sulfo fatty acid ester salt, an α-acyl sulfonate, an alkyl sulfonate, an alkene sulfonate, a sulfonate of a fatty acid ester, a sulfonate of a fatty acid amide, an alkyl sulfonate and a sulfonate of its formalin condensate, an alkyl sulfate ester salt, a sulfate ester salt of a secondary alcohol, a sulfate ester salt of an alkyl and an allyl ether, a sulfate salt of a fatty acid ester, a sulfate salt of a fatty acid alkylolamide, a sulfate salt of a Turkey red oil and so on, an alkyl phosphate salt, an alkenyl phosphate salt, an ether phosphate salt, an alkyl allyl ether phosphate salt, an alkyl amide phosphate salt, and an N-acylamino acid.

Illustrative example of the cationic surfactant includes an alkyl amine salt, an amine salt such as between a fatty acid derivative and a polyamine or an amino alcohol, an alkyl quaternary ammonium salt, an aromatic quaternary ammonium salt, a pyridinium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytosterol ether, a polyoxyethylene phytosterol ether, a polyoxyethylene cholestanol ether, a polyoxyethylene cholesteryl ether, a polyoxyalkylene-modified organopolysiloxane, an organopolysiloxane co-modified with a polyoxyalkylene and an alkyl, an organopolysiloxane co-modified with a polyoxyalkylene and a fluoroalkyl, a block copolymer of a polyoxyalkylene and an organopolysiloxane, an alkanol amide, a sugar ether, and a sugar amide.

Illustrative example of the amphoteric surfactant includes a betaine, an aminocarboxylic acid salt, and an imidazoline derivative.

iii) Crosslinking Organopolysiloxane

The cosmetic of the present invention may contain one, or two or more kinds of crosslinking organopolysiloxanes, depending on the purpose thereof. It is preferable that this crosslinking organopolysiloxane swell by absorbing a low viscous silicone having viscosity of 0.65 to 10.0 mm$^2$/sec (25° C.), the amount of which is more than own weight of the crosslinking organopolysiloxane. It is preferable that the crosslinking organopolysiloxane have two or more reactive vinyl moieties in its molecular structure and form a crosslinking structure by reacting with a hydrogen atom directly bonded to a silicon atom. The crosslinking organopolysiloxane preferably contains at least one kind selected from the group consisting of a polyoxyalkylene moiety, an alkyl moiety, an alkenyl moiety, an aryl moiety, and a fluoroalkyl moiety. Amount of the crosslinking organopolysiloxane to be blended is preferably in the range of 0.1 to 30% by mass, and particularly 1 to 10% by mass, relative to the total amount of the cosmetic.

Iv) A Silicone Resin Such as a Graft or a Block Copolymer of an Acryl and a Silicone, and a Net-work Silicone Compound The cosmetic of the present invention may contain, depending on the purpose thereof, one, or two or more silicone resins selected a graft or a block copolymer of an acryl and a silicone, and a net-work silicone compound. In particular, the silicone resin is preferably an acryl silicone resin in the present invention. The silicone resin is preferably an acryl silicone resin containing at least one kind selected from the group consisting of a pyrrolidone moiety, a long chain alkyl moiety, a polyoxyalkylene moiety, and a fluoroalkyl moiety. Further, the silicone resin is preferably a net-work silicone compound. Amount of the silicone resin to be blended, such as a graft or a block copolymer of an acryl, and a net-work silicone compound, is preferably in the range of 0.1 to 20% by mass, particularly 1 to 10% by mass, relative to the total amount of the cosmetic.

The cosmetic of the present invention can be added with a component other than the compound; illustrative example thereof includes a water-soluble polymer, a film-forming agent, an oil-soluble gelation agent, an organic modified clay mineral, a resin, a UV absorbing-scattering agent, a moisturizer, a preservative, an antibacterial agent, a fragrance, a salt, an antioxidant, a pH controller, a chelating agent, an algefacient, an anti-inflammatory agent, a skin care component, a vitamin, an amino acid, a nucleic acid, a hormone, and a clathrate compound.

Preferable specific example of the cosmetic of the present invention includes a skin care cosmetic, a make-up cosmetic, a hair cosmetic, and an ultraviolet protective cosmetic. The product is not particularly restricted in the form, but can be in the form of a liquid, a milky lotion, a cream, a solid, a paste, a gel, a powder, a multilayer, a mousse, a spray and so on.

Specific example of the cosmetic of the present invention includes a hair cosmetic. The block type organosiloxane of the present invention can provide a hair cosmetic excellent in emulsion stability and temporal stability as a surfactant by containing the block type organosiloxane as a surfactant in the hair cosmetic. The content of the block type organopolysiloxane of the present invention in the hair cosmetic is preferably in the range of 0.1 to 20% by mass in view of a favorable reviving property and ensured sustainability, more preferably 1 to 10% by mass, and much more preferably 1 to 5% by mass.

An oil material, in particular, having a conditioning property to hair may be further blended into the hair cosmetic of the present invention. Illustrative example of the oil material can be one or more kinds of a silicone selected from a lower alcohol, a saturated or an unsaturated alcohol having 12 to 30 carbon atoms; an ether of the alcohol and a polyvalent alcohol; an ester of the alcohol and a fatty acid having 1 to 11 carbon atoms; a saturated or an unsaturated fatty acid having 12 to 30 carbon atoms; an ester of the fatty acid and a monovalent or a polyvalent alcohol; an amide of the fatty acid and an amine; a sterol; a squalene; a phospholipid; a glycolipid; an animal oil; a vegetable oil; a cyclic, a linear, or a branched dimethyl polysiloxane, a methyl polysiloxane, a polysiloxane, an alkyl-modified silicone, a methylphenyl polysiloxane, and a polyether-modified silicone.

Amount of the oil material to be blended into the hair cosmetic is preferably in the range of 0.01 to 30% by mass, more preferably 1 to 25% by mass, and much more preferably 3 to 20% by mass.

Furthermore, a thickner such as a hydroxyethyl cellulose, a surfactant, an anionic, an amphoteric, a cationic, and a nonionic polymer, a fragrance, a pearlescent aid, a polymer for hair setting, a pigment, a UV absorbing-scattering agent, an antioxidant, and a preservative may be blended into the hair cosmetic of the present invention as appropriate.

The surfactant is not particularly restricted if it is used for a normal hair cosmetic, and any of an anionic surfactant, a nonionic surfactant, an amphoteric surfactant, and a cationic surfactant can be desirably used.

Specific example of the anionic surfactant includes an alkyl benzene sulfonate, preferably a linear- or a branched-chain alkyl benzene sulfonate having an alkyl group having 10 to 16 average carbon atoms; an alkyl ether sulfate salt or an alkenyl ether sulfate salt, preferably an alkyl ether sulfate salt or an alkenyl ether sulfate salt having a linear- or a branched-chain alkyl group or an alkenyl group having 10 to 20 average carbon atoms to which an ethylene oxide/propylene oxide/butylene oxide/ethylene oxide and a propylene oxide (0.5 to 8 moles in one molecular structure) are added with a molar ratio of 0.1/9.9 to 9.9/0.1 and an ethylene oxide and a butylene oxide (0.5 to 8 moles in one molecular structure) are added with a molar ratio of 0.1/9.9 to 9.9/0.1; an alkyl sulfate salt or an alkenyl sulfate salt, and preferably an alkyl sulfate salt or an alkenyl sulfate salt having an alkyl group or an alkenyl group having 10 to 20 average carbon atoms; an olefin sulfonate, and preferably an olefin sulfonate having 10 to 20 average carbon atoms in one molecular structure; an alkane sulfonate and preferably an alkane sulfonate having 10 to 20 average carbon atoms in one molecular structure; a higher fatty acid salt, and preferably a saturated or an unsaturated fatty acid salt having 10 to 24 average carbon atoms in one molecular structure; (amide) ether carboxylic acid type surfactant; an α-sulfo fatty acid salt or an α-sulfo fatty acid ester, and preferably an α-sulfo fatty acid salt or an α-sulfo fatty acid ester having an alkyl group or an alkenyl group having 10 to 20 average carbon atoms; an N-acyl amino acid type surfactant, and preferably an N-acyl amino acid type surfactant having an acyl group and a free carboxylic acid residue having 8 to 24 carbon atoms (e.g. an N-acyl sarcosinate, an N-acyl-β-alanine); a phosphoric ester type surfactant, and preferably a phosphoric monoester or a diester type surfactant having an alkyl group, an alkenyl group or an alkylene oxide adduct thereof having 8 to 24 carbon atoms; a sulfosuccinate type surfactant, and preferably a sulfosuccinate such as a higher alcohol having 8 to 22 carbon atoms or an ethoxylate thereof or a higher fatty acid amide-derived sulfosuccinate; a polyoxyalkylenefatty acid amide ether sulfate salt, and preferably a sulfate salt such as a linear- or a branched-chain saturated or unsaturated fatty acid monoethanol amide having 8 to 24 carbon atoms and an ethoxylate of a diethanol amide; a monoglyceride sulfate ester salt, and preferably a monoglyceride sulfate ester salt having a fatty acid group of a linear- or a branched-chain saturated or unsaturated having 8 to 24 carbon atoms; an acylated isethionate, and preferably an acylated isethionate having a linear- or a branched-chain saturated or unsaturated fatty acid group having 8 to 24 carbon atoms; an alkyl glyceryl ether sulfate salt or an alkyl glyceryl ether sulfonate, and preferably an alkyl glyceryl ether sulfate salt or an alkyl glyceryl ether sulfonate having a linear or a branched-chain alkyl group or an alkenyl group having 8 to 24 carbon atoms or an alkylene oxide adduct thereof; an alkyl or an alkenyl amide sulfonate, and preferably an alkyl or an alkenyl amide sulfonate having a linear- or a branched-chain alkyl group or alkenyl group having 8 to 24 carbon atoms; an alkanolamide sulfosuccinate, and preferably an alkanolamide sulfosuccinate having a linear- or a branched-chain alkyl group or an alkenyl group having 8 to 24 carbon atoms; an alkyl sulfoacetate, and preferably an alkyl sulfoacetate having a linear- or a branched-chain alkyl group or an alkenyl group having 8 to 24 carbon atoms; an acylated taurate, and preferably an acyl taurate having a linear- or a branched-chain saturated or unsaturated fatty acid group having 8 to 24 carbon atoms; N-acyl-N-carboxyethyl glycine salt, and preferably an N-acyl-N-carboxyethyl glycine salt having an acyl group having 6 to 24 carbon atoms.

Illustrative example of the salt of the anionic surfactant, or the counterion of the anionic residue includes an alkali metal ion such as sodium and potassium; an alkaline earth metal ion such as calcium and magnesium; an ammonium ion, and an alkanolamine having 1 to 3 alkanol groups having 2 or 3 carbon atoms (e.g. monoethanol amine, diethanol amine, triethanol amine, and triisopropanol amine).

Preferable example of the above anionic surfactant includes an alkyl ether sulfate salt, and particularly a polyoxyethylenealkyl ether sulfate salt.

Illustrative example of the nonionic surfactant includes a polyoxyalkylenealkylether or a polyoxyalkylenealkenylether having e.g. a linear- or a branched-chain alkyl group or an alkenyl group having 10 to 24 average carbon atoms to which an ethylene oxide, a propylene oxide or a butylene oxide is added; a glycerin ester of a fatty acid having 8 to 20 carbon atoms; a glycol ester of a fatty acid having 8 to 20 carbon atoms; an alkylene oxide adduct of a monoglyceride of a fatty acid having 8 to 20 carbon atoms; a sucrose ester of a fatty acid having 8 to 20 carbon atoms; a sorbitan ester of a fatty acid having 8 to 20 carbon atoms; a polyglycerin fatty acid ester having an acyl group having 8 to 20 carbon atoms; a monoethanol amide or a diethanol amide of a fatty acid having 8 to 20 carbon atoms or an ethoxylate thereof; a polyoxyethylene cured castor oil; a polyoxyalkylenesorbitan fatty acid ester having an acyl group having 8 to 20 carbon atoms; a polyoxyethylene sorbit fatty acid ester having an acyl group having 8 to 20 carbon atoms; an alkylsaccharide surfactant having a linear- or a branched-chain alkyl group, an alkenyl group or an alkylphenyl group having 8 to 18 carbon atoms; an alkyl amine oxide or an alkyl amide amine oxide having a linear- or a branched-chain alkyl group or an alkenyl group having 8 to 20 carbon atoms; an ether compound or an ester compound of a polyvalent alcohol having a linear- or a branched-chain alkyl group or an alkenyl group having 8 to 20 carbon atoms; a polyoxyalkylene-modified organopolysiloxane, an organopolysiloxane co-modified with a polyoxyalkylene and an alkyl, a polyglycerin-modified organopolysiloxane, an organopolysiloxane co-modified with a polyglycerin and an alkyl, an organopolysiloxane co-modified with a polyoxyalkylene and a fluoroalkyl, a crosslinking polyoxyalkylene and organopolysiloxane, a sugar-modified silicone, an oxazoline-modified silicone, a polyoxyalkylenealkylaryl ether, a polyoxyalkylene lanolin alcohol, a polyoxyalkylene fatty acid ester, a pluronic block polymer, a tetronic block polymer, a polyoxyalkylene fatty acid amide, a polyoxyalkylenealkyl amide, and a polyethyleneimine derivative.

Illustrative example of the amphoteric surfactant includes an amide amino-type, carbo betaine-type, an amide betaine-type, a sulfo betaine-type, an amide sulfobetaine-type, an imidazolinium betaine-type, an amino acid-type, a phospho betaine-type, and a phosphoric ester-type.

Illustrative example of the cationic surfactant includes a tertiary amine, a quaternary ammonium salt, an amide amine, and an ester amine, specifically a behenyl trimethyl ammonium chloride, a distearyldimethyl ammonium chloride, a cetyltrimethyl ammonium chloride, a stearyltrimethyl ammonium chloride, a lauryltrimethyl ammonium chloride, an N-stearyl N—N—N-tri(polyoxyethylene) ammonium chloride (3 mole of an ethylene oxide added in total), a cetyl-benzyldimethyl ammonium chloride, a cetyltriethyl ammonium bromide, a distearyldimethyl ammonium chloride, and a 2-decyltetradecyltrimethyl ammonium chloride, a 2-dodecylhexadecyltrimethyl ammonium chloride, a di-2-hexyldecyldimethyl ammonium chloride, a di-2-octyldodecyldimethyl ammonium chloride, a behenyl tertiary amine, a stearyl tertiary amine, and a stearamidepropyl dimethylamine.

One, or two or more kinds of the surfactant can be used, preferably in the range of 0.1 to 50% by mass blended into the hair cosmetic, and further 0.5 to 40% by mass, particularly 1 to 30% by mass to be blended to provide excellent foaming property.

If the hair cosmetic of the present invention is in the form of a hair-set composition, a hair form agent, or a hair spray agent, and so on, illustrative example of the polymer for hair setting includes a polyvinyl pyrrolidone and a polymer thereof (a polyvinyl pyrrolidone/vinyl acetate copolymer, a polyvinyl pyrrolidone/vinyl acetate/vinyl propionate crosslinking copolymer, a polyvinyl pyrrolidone/alkylamino acrylate copolymer, a polyvinyl pyrrolidone/acrylate/(metha) acrylic copolymer, a polyvinyl pyrrolidone/alkylaminoacrylate/vinyl caprolactam copolymer), a methylvinyl ether/maleic anhydride alkyl half ester copolymer, a polymer of a vinyl acetate (a vinyl acetate/crotonic acid copolymer, a vinyl acetate/crotonic acid/vinyl neodecanoate copolymer, a vinyl acetate/crotonic acid/vinyl propionate copolymer, a vinyl acetate/tert-butyl benzoic acid vinyl/crotonic acid copolymer, a (metha) acrylic acid/(metha) acrylic ester copolymer), a polymer acrylate (an acrylic acid/alkylester acrylate/alkyl acrylamide copolymer, a (metha) acryl ethyl betaine/(metha) alkylester acrylate copolymer, a copolymer of an N-methacryloyloxyethyl-N,N-dimethyl ammonium α-N-methylcarboxybetaine and a (metha) alkylester acrylate, an alkylester acrylate/methacrylic acid butylaminoethyl/acrylic acid octylamide copolymer), a basic acrylic polymer compound, a compound having a cellulose skeleton, a cationic cellulose derivative, a salt of a monovalent acid such as a hydroxypropyl chitosan, a carboxymethylchitin, a carboxymethyl chitosan, a chitosan, a pyrrolidone carboxylate, a lactic acid, and a glycolic acid, and a divalent acid such as an adipic acid and a succinic acid, and a water-dispersible polyester.

One, or two or more kinds of the polymer for hair setting can be used. Amount of the polymer for hair setting in the hair cosmetic is preferably in the range of 0.1 to 10% by mass, more preferably 0.5 to 6% by mass, and particularly 1 to 4% by mass in order to obtain necessary and sufficient hair setting force.

Illustrative example of the hair cosmetic includes a hair shampoo, a hair treatment, and a hair conditioner used in the bathroom, and a hair form, a hair spray, a hair cream, a hair wax, and a hair gel used outside the bathroom, and an agent used at home or a beauty salon for beauty treatment such as a hair dye, a permanent wave agent, a hair manicure, and a hair bleach. The organopolysiloxane of the present invention can be blended into any of these agents.

EXAMPLES

Hereinafter, the present invention will be described in detail with reference to Preparation Examples, Comparative Preparation Examples, Examples and Comparative Examples, but is not limited to the following Examples. The data in the following table are converted in terms of pure components, unless otherwise indicated. The kinematic viscosity is measured at 25° C. by using an Ostwald viscometer, and the degree of viscosity is measured at 25° C. by using a rotational viscometer (DV-II+: Product from Brookfield Corporation). The average molecular weight is defined as weight average molecular weight in terms of polystyrene by gel permination chromatography (GPC).

Preparation Example 1

Into a reactor were charged 100 parts by mass of an organohydrogen polysiloxane represented by the following general formula with a kinematic viscosity of 17 mm$^2$/s (25° C.),

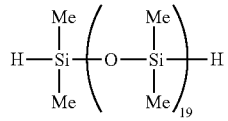

30 parts by mass of a 2-propanol, 42 parts by mass of a polyoxyalkylene compound represented by the following general formula with a vinyl valency of 3.28 mmol/g, and 0.01 parts by mass of a 1-butanol solution containing chloroplatinic acid (platinum: 3% by mass); and agitated at 80° C. for 4 hours,

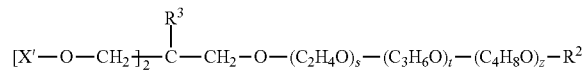

wherein X'=CH$_2$—CH—CH$_2$—, R$^2$=—H, R$^3$=—CH$_2$—CH$_3$, s=9, t=0, and z=0

Part of the reaction mixture was extracted.

Thereafter, the infrared absorption spectrum and the $^1$HNMR spectrum were measured by using Fourier transform infrared spectroscopy (FT-IR: Product from Thermo Fisher Scientific K.K.) and a CDCl3 solvent (Product from Bruker Optics K.K., at 400 MHz), respectively, to confirm the disappearance of an Si—H-derived peak and the reaction was completed.

The reaction mixture obtained was heated under reduced pressure at 120° C. to distill the solvent out to obtain a clear, colorless polyoxyalkylene-modified organopolysiloxane represented by the following formula with a degree of viscosity of 8000 mPa·s (25° C.) and an average molecular weight of 15000,

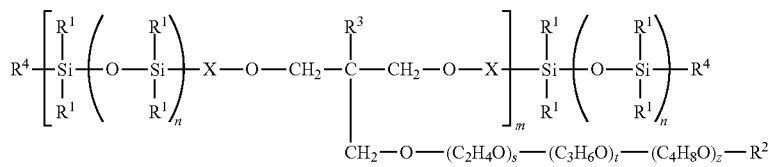

R$^1$=—CH$_3$
R$^2$=—H
R$^3$=—CH$_2$—CH$_3$
X=—CH$_2$—CH$_2$—CH$_2$— n=19
m=6
s=9
t=0
z=0
R$^4$=the following general formula

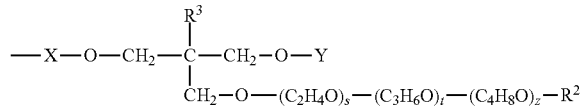

wherein X, R$^2$, R$^3$, s, t, and z are the same as before, and Y=—CH=CH—CH$_3$ Preparation Example 2

Into a reactor were charged 150 parts by mass of an organohydrogen polysiloxane represented by the following general formula with a kinematic viscosity of 35 mm$^2$/s (25° C.),

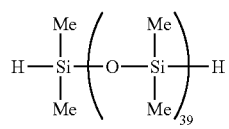

30 parts by mass of a 2-propanol, 110 parts by mass of a polyoxyalkylene compound represented by the following general formula with a vinyl valency of 0.971 mmol/g, and 0.01 parts by mass of a 1-butanol solution containing chloroplatinic acid (platinum: 3% by mass); and agitated at 80° C. for 5 hours.

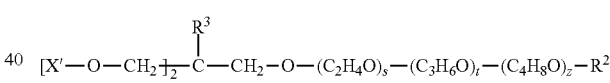

wherein X'=CH$_2$=CH—CH$_2$—, R$^2$=—H, R$^3$=—CH$_2$—CH$_3$, s=18, t=18, and z=0

Part of the reaction mixture was extracted. Thereafter, the infrared absorption spectrum and the $^1$HNMR spectrum were measured by using Fourier transform infrared spectroscopy (FT-IR: Product from Thermo Fisher Scientific K.K.) and a CDCl$_3$ solvent (Product from Bruker Optics K.K., at 400 MHz), respectively, to confirm the disappearance of an Si—H-derived peak and the reaction was completed.

The reaction mixture obtained was heated under reduced pressure at 110° C. to distill the solvent out to obtain a clear, colorless polyoxyalkylene-modified organopolysiloxane represented by the following formula with a degree of viscosity of 7800 mPa·s (25° C.) and an average molecular weight of 27000.

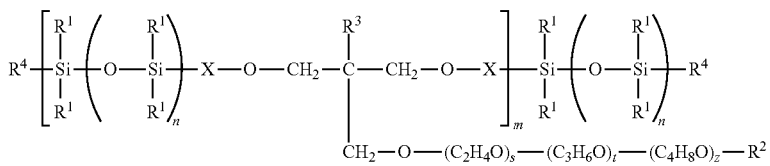

$R^1$=—$CH_3$
$R^2$=—H
$R^3$=—$CH_2$—$CH_3$
X=—$CH_2$—$CH_2$—$CH_2$
n=39
m=4
s=18
t=18
z=0
$R^4$=the following general formula

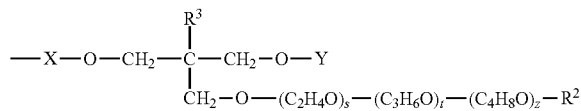

wherein X, $R^2$, $R^3$, s, t, and z are the same as before, and Y=—CH=CH—$CH_3$

Preparation Example 3

Into a reactor were charged 200 parts by mass of an organohydrogen polysiloxane represented by the following general formula with a kinematic viscosity of 76 mm²/s (25° C.),

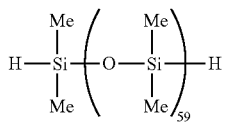

50 parts by mass of an ethyl alcohol, 29 parts by mass of a polyoxyalkylene compound represented by the following general formula with a vinyl valency of 3.28 mmol/g, and 0.02 parts by mass of a 1-butanol solution containing chloroplatinic acid (platinum: 3% by mass); and agitated at 80° C. for 6 hours,

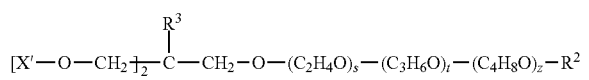

wherein X'=—$CH_2$=CH—$CH_2$—, $R^2$=—H, $R^3$=—$CH_2$—$CH_3$, s=9, t=0, and z=0

Part of the reaction mixture was extracted. Thereafter, the infrared absorption spectrum and the ¹HNMR spectrum were measured by using Fourier transform infrared spectroscopy (FT-IR: Product from Thermo Fisher Scientific K.K.) and a CDCl₃ solvent (Product from Bruker Optics K.K., at 400 MHz), respectively, to confirm the disappearance of an Si—H-derived peak and the reaction was completed.

The reaction mixture obtained was heated under reduced pressure at 110° C. to distill the solvent out to obtain a clear, colorless polyoxyalkylene-modified organopolysiloxane represented by the following formula with a degree of viscosity of 39100 mPa·s (25° C.) and an average molecular weight of 65500.

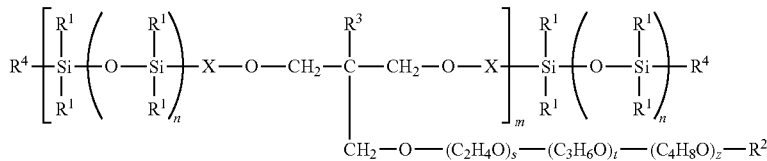

$R^1$=—$CH_3$
$R^2$=—H
$R^3$=—$CH_2$—$CH_3$
X=—$CH_2$—$CH_2$—$CH_2$—
n=59
m=12
s=9
t=0
z=0
$R^4$=the following general formula, and part thereof is —O—$CH_2$—$CH_3$

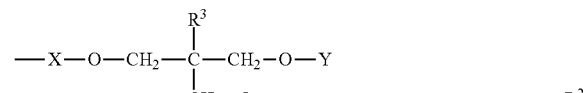

wherein X, $R^2$, $R^3$ s, t, and z are the same as before, and Y=—CH=CH—$CH_3$

Preparation Example 4

Into a reactor were charged kinematic 100 parts by mass of an organohydrogen polysiloxane represented by the following general formula with a viscosity of 98 mm²/s (25° C.),

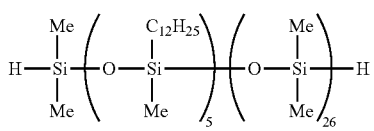

40 parts by mass of a 2-propanol, 18 parts by mass of a polyoxyalkylene compound represented by the following general formula with a vinyl valency of 3.74 mmol/g, and 0.01 parts by mass of a 1-butanol solution containing chloroplatinic acid (platinum: 3% by mass); and agitated at 85° C. for 6 hours,

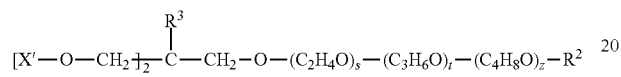

wherein $X'=CH_2=C(CH_3)—CH_2—$, $R^2=—H$, $R^3=—CH_2—CH_3$, $s=5$, $t=0$, and $z=1$ Part of the reaction mixture was extracted. Thereafter, the infrared absorption spectrum and the $^1HNMR$ spectrum were measured by using Fourier transform infrared spectroscopy (FT-IR: Product from Thermo Fisher Scientific K.K.) and a $CDCl_3$ solvent (Product from Bruker Optics K.K., at 400 MHz), respectively, to confirm the disappearance of an Si—H-derived peak and the reaction was completed.

The reaction mixture obtained was heated under reduced pressure at 110° C. to distill the solvent out to obtain a clear, colorless polyoxyalkylene-modified organopolysiloxane represented by the following formula with a degree of viscosity of 566000 mPa·s (25° C.) and an average molecular weight of 105500.

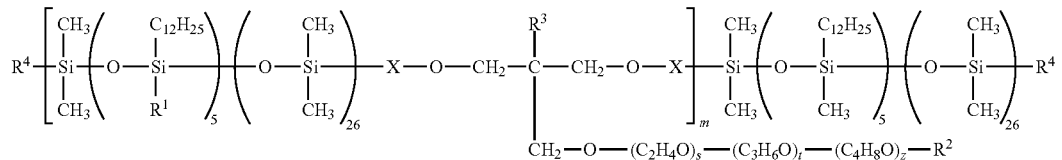

$R^2=—H$
$R^3=—CH_2—CH_3$
$X=—CH_2—CH(CH_3)—CH_2—$
$m=28$
$s=5$
$t=0$
$z=1$
$R^4=$the following general formula

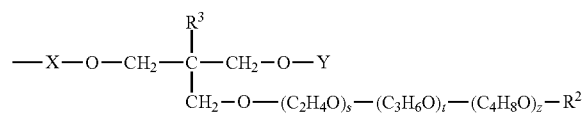

wherein X, $R^2$, $R^3$, s, t, and z are the same as before, and $Y=CH_2=C(CH_3)—CH_2—$ Preparation Example 5

Into a reactor were charged 150 parts by mass of an organohydrogen polysiloxane represented by the following general formula with a kinematic viscosity of 240 mm²/s (25° C.),

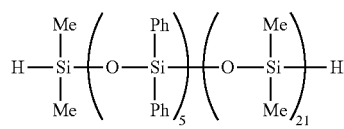

50 parts by mass of a toluene, 84 parts by mass of a polyoxyalkylene compound represented by the following general formula with a vinyl valency of 3.28 mmol/g, and 0.06 parts by mass of a toluene solution containing chloroplatinic acid (platinum: 0.5% by mass); and agitated at 115° C. for 5 hours,

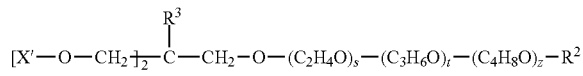

wherein $X'=CH_2=CH—CH_2—$, $R^2=—H$, $R^3=—CH_2—CH_3$, $s=9$, $t=0$, and $z=0$

Part of the reaction mixture was extracted. Thereafter, the infrared absorption spectrum and the $^1HNMR$ spectrum were measured by using Fourier transform infrared spectroscopy (FT-IR: Product from Thermo Fisher Scientific K.K.) and a $CDCl_3$ solvent (Product from Bruker Optics K.K., at 400 MHz), respectively, to confirm the disappearance of an Si—H-derived peak and the reaction was completed.

The reaction mixture obtained was heated under reduced pressure at 130° C. to distill the solvent out to obtain a clear, colorless polyoxyalkylene-modified organopolysiloxane represented by the following formula with a degree of viscosity of 36000 mPa·s (25° C.) and an average molecular weight of 26000.

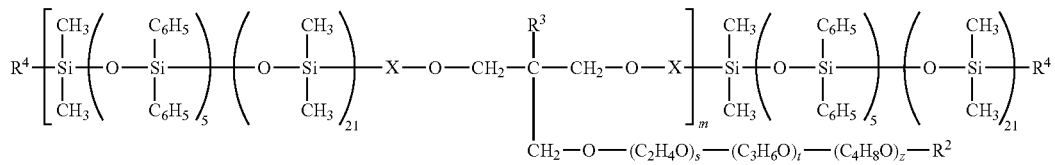

$R^2$=—H
$R^3$=—$CH_2$—$CH_3$
X=—$CH_2$—$CH_2$—$CH_2$—
m=7
s=9
t=0
z=0
$R^4$=the following general formula

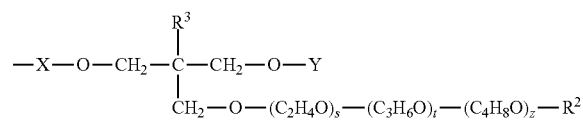

wherein X, $R^2$, $R^3$, s, t, and z are the same as before, and
Y=—CH—CH=$CH_3$

Preparation Example 6

Into a reactor were charged 300 parts by mass of an organohydrogen polysiloxane represented by the following general formula with a kinematic viscosity of 2530 mm²/s (25° C.),

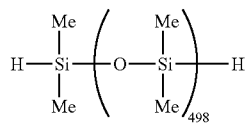

100 parts by mass of a 2-propanol, 2.9 parts by mass of a polyoxyalkylene compound represented by the following general formula with a vinyl valency of 6.62 mmol/g, and 0.05 parts by mass of a 1-butanol solution containing chloroplatinic acid (platinum: 3% by mass); and agitated at 80° C. for 6 hours,

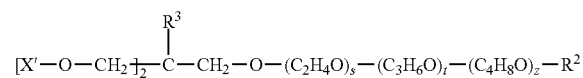

wherein X'=$CH_2$—CH—$CH_2$—, $R^2$=—H, $R^3$=—$CH_2$—$CH_3$, s=2, t=0, and z=0

Part of the reaction mixture was extracted. Thereafter, the infrared absorption spectrum and the ¹HNMR spectrum were measured by using Fourier transform infrared spectroscopy (FT-IR: Product from Thermo Fisher Scientific K.K.) and a $CDCl_3$ solvent (Product from Bruker Optics K.K., at 400 MHz), respectively, to confirm the disappearance of an Si—H-derived peak and the reaction was completed.

The reaction mixture obtained was heated under reduced pressure at 110° C. to distill the solvent out to obtain a clear, slightly yellow polyoxyalkylene-modified organopolysiloxane represented by the following formula with a degree of viscosity of 1040000 mPa·s (25° C.) and an average molecular weight of 560000.

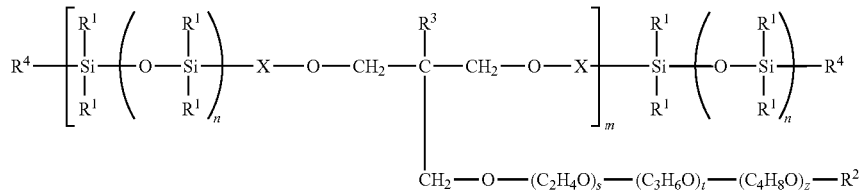

$R^1$=—$CH_3$
$R^2$=—H
$R^3$=—$CH_2$—$CH_3$
X=—$CH_2$—$CH_2$—$CH_2$—
n=498
m=14
s=2
t=0
z=0
$R^4$=the following general formula

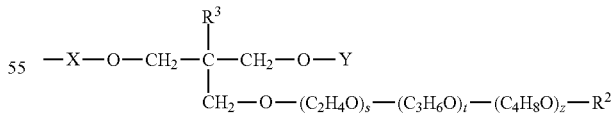

wherein X, $R^2$, $R^3$, s, t, and z are the same as before, and
Y=—CH—CH=$CH_3$.

Comparative Preparation Example 1

Into a reactor were charged 100 parts by mass of an organohydrogen polysiloxane represented by the following general formula with a kinematic viscosity of 17 mm²/s (25° C.),

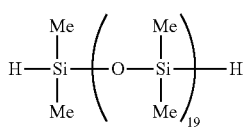

30 parts by mass of a 2-propanol, 35 parts by mass of a polyoxyalkylene compound represented by the following general formula with a vinyl valency of 3.92 mmol/g, and 0.01 parts by mass of a 1-butanol solution containing chloroplatinic acid (platinum: 3% by mass); and agitated at 80° C. for 4 hours.

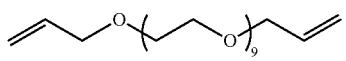

Part of the reaction mixture was extracted. Thereafter, the infrared absorption spectrum and the $^1$HNMR spectrum were measured by using Fourier transform infrared spectroscopy (FT-IR: Product from Thermo Fisher Scientific K.K.) and a CDCl$_3$ solvent (Product from Bruker Optics K.K., at 400 MHz), respectively, to confirm the disappearance of an Si—H-derived peak and the reaction was completed.

The reaction mixture obtained was heated under reduced pressure at 120° C. to distill the solvent out to obtain a clear, colorless polyoxyalkylene-modified organopolysiloxane represented by the following formula with a degree of viscosity of 12000 mPa·s (25° C.) and an average molecular weight of 16000.

Examples 1 to 4 and Comparative Examples 1 to 6

By using the polyoxyalkylene-modified organopolysiloxanes above prepared in Preparation Examples 1, 3, and 4, and Comparative Preparation Example 1 according to a conventional method, water-in-oil milky lotions with the components as shown in the following Table 1 (in % by mass) were prepared as Examples and Comparative Examples (Examples 1 to 4, and Comparative Examples 1 to 6). The milky lotions obtained were evaluated according to the following methods. The results are shown in the following Table 1.

(Evaluation Method)

The emulsion stability of the milky lotions as shown in Table 1 were visually evaluated at 50° C. one and 3 months after application.

The evaluation criteria are described as follows.
Very good: No separation was observed.
Good: Slight separation was observed.
Fair: Separation was observed.
Bad: Separation into two phases was observed.

Additional sensory evaluation was made as to each of the milky lotions by using 5 panelists. 2 g of each of the milky lotions was applied to the skin thereof and fitted well to evaluate non-stickiness, light feeling of applied lotion, and light spreading properties. The data are classified according to the number of the panelists who found the milky lotion "usable," as shown in the following evaluation criteria.

(Evaluation Criteria)
Very good: 4 to 5 panelists
Good: 3 panelists
Fair: 2 panelists
Bad: 1 or no panelist

TABLE 1

| | | Example | | | | Comparative Example | | | | | |
|---|---|---|---|---|---|---|---|---|---|---|---|
| | | 1 | 2 | 3 | 4 | 1 | 2 | 3 | 4 | 5 | 6 |
| 1 | Polyoxyalkylene-modified organopolysiloxane of Preparation Example 1 | 2 | | | | | | | | | |
| 2 | Polyoxyalkylene-modified organopolysiloxane of Preparation Example 3 | | 2 | | | | | | | | |
| 3 | Polyoxyalkylene-modified organopolysiloxane of Preparation Example 4 | | | 2 | 2 | | | | | | |
| 4 | Polyoxyalkylene-modified organopolysiloxane of Comparative Preparation Example 1 | | | | | 2 | | | | 2 | |
| 5 | KF-6017 *1 | | | | | | 2 | | | | 2 |
| 6 | FZ-2233 *2 | | | | | | | 2 | | | |
| 7 | KF-6050 *3 | | | | | | | | 2 | | |
| 8 | Decamethylcyclopentasiloxane | 12 | 12 | 8 | 8 | 12 | 12 | 12 | 12 | 8 | 8 |
| 9 | Dimethylpolysiloxane (6 mm$^2$/s) | 9 | 9 | 9 | 6 | 9 | 9 | 9 | 9 | 9 | 6 |
| 10 | Squalane | 2 | 2 | | | 2 | 2 | 2 | 2 | | |
| 11 | Mineral oil | | | 6 | | | | | | 6 | |
| 12 | Isododecane | | | | 8 | | | | | | 8 |
| 13 | 1,3-butylene glycol | 5 | 5 | 5 | 5 | 5 | 5 | 5 | 5 | 5 | 5 |
| 14 | Sodium citrate | 0.2 | 0.2 | 0.2 | 0.2 | 0.2 | 0.2 | 0.2 | 0.2 | 0.2 | 0.2 |
| 15 | Sodium chloride | 0.2 | 0.2 | 0.2 | 0.2 | 0.2 | 0.2 | 0.2 | 0.2 | 0.2 | 0.2 |
| 16 | Ethanol | 2 | 2 | 2 | 2 | 2 | 2 | 2 | 2 | 2 | 2 |
| 17 | Purified water | Rest | Rest | Rest | Rest | Rest | Rest | Rest | Rest | Rest | Rest |
| Evaluation | Emulsion stability at 50° C. one month after application | Very good | Very good | Very good | Very good | Good | Good | Very good | Good | Fair | Fair |

TABLE 1-continued

|  | Example | | | | Comparative Example | | | | | |
| --- | --- | --- | --- | --- | --- | --- | --- | --- | --- | --- |
|  | 1 | 2 | 3 | 4 | 1 | 2 | 3 | 4 | 5 | 6 |
| Emulsion stability at 50° C. 3 months after application | Very good | Very good | Very good | Good | Fair | Fair | Good | Fair | Fair | Fair |
| Non-stickiness | Very good | Good | Very good | Good | Fair | Good | Bad | Fair | Fair | Good |
| Light feeling when applied | Very good | Good | Good | Very good | Fair | Good | Fair | Fair | Fair | Good |
| Favorable spreading property | Very good | Good | Good | Very good | Fair | Very good | Fair | Fair | Good | Good |

*1 KF-6017: Pendant-type polyether-modified silicone (Product from Shin-Etsu Chemical Co., Ltd.)
*2 FZ-2233: Linear block polyether-modified silicone (Product from Dow Corning Toray Co., Ltd.)
*3 KF-6050: High-polymerization pendant-type polyether-modified silicone (Product from Shin-Etsu Chemical Co., Ltd.)

As shown in Table 1, the milky lotions of Examples 1 to 4 exhibited high temporal emulsification stability, non-stickiness, light spreading properties and light feeling, as opposed to the milky lotions of Comparative Examples 1 to 6.

Each cosmetic was prepared according to a conventional method to make a sensory evaluation.

| Example 5: Hair treatment | |
| --- | --- |
| (Components) | % by mass |
| Octadecyloxy(2-hydroxypropyl)dimethylamine | 0.5 |
| Stearic acid dimethylaminopropylamide | 2.0 |
| Stearyl alcohol | 5.0 |
| Dipropylene glycol | 1.0 |
| Benzyl alcohol | 0.5 |
| Phenoxyethanol | 0.1 |
| Polyoxyalkylene-modified organopolysiloxane of Preparation Example 6 | 2.5 |
| High-polymerization dimethyl polysiloxane (note) | 0.5 |
| Glycerin | 5.0 |
| Polypropylene glycol | 2.5 |
| Lanolin fatty acid | 0.5 |
| Sunflower seed oil | 0.5 |
| Lactic acid | 1.5 |
| Fragrance | 0.4 |
| Sodium hydroxide | 0.1 |
| Ion-exchanged ion | Remainder |

(note): KF-96H 100000cs (Product from Shin-Etsu Chemical Co., Ltd.)

The hair treatment thus obtained exhibited favorable smooth, soft, and combable feelings without temporal change or stickiness.

| Comparative Example 7: Hair treatment | |
| --- | --- |
| (Components) | % by mass |
| Octadecyloxy(2-hydroxypropyl)dimethylamine | 0.5 |
| Stearic acid dimethylaminopropylamide | 2.0 |
| Stearyl alcohol | 5.0 |
| Dipropylene glycol | 1.0 |
| Benzyl alcohol | 0.5 |
| Phenoxyethanol | 0.1 |
| Polyoxyalkylene-modified organopolysiloxane of Comparative Preparation Example 1 | 2.5 |
| High-polymerization dimethyl polysiloxane (note) | 0.5 |
| Glycerin | 5.0 |
| Polypropylene glycol | 2.5 |
| Lanolin fatty acid | 0.5 |
| Sunflower seed oil | 0.5 |
| Lactic acid | 1.5 |
| Fragrance | 0.4 |
| Sodium hydroxide | 0.1 |
| Ion-exchanged ion | Remainder |

(note): KF-96H 100000cs (Product from Shin-Etsu Chemical Co., Ltd.)

The hair treatment thus obtained exhibited temporal change in emulsion particle size, stickiness in application, and unfavorable combable feeling.

| Example 6: Lipstick | |
| --- | --- |
| (Components) | % by mass |
| Candelilla wax | 8.0 |
| Polyethylene wax | 8.0 |
| Long chain alkyl-containing acryl silicone resin (note 1) | 12.0 |
| Methylphenyl polysiloxane (note 2) | 3.0 |
| Isotridecyl isononanoate | 20.0 |
| Glyceryl isostearate | 16.0 |
| Polyoxyalkylene-modified organopolysiloxane of Preparation Example 4 | 1.0 |
| Octadecyldimethylbenzyl ammonium salt-modified montmorillonite | 0.5 |
| Polyglyceryl triisostearate | 27.0 |
| Silicone-treated Red No. 202 (note 3) | 0.8 |
| Silicone-treated colcothar (note 3) | 1.3 |
| Silicone-treated yellow iron oxide (note 3) | 1.0 |
| Silicone-treated black iron oxide (note 3) | 0.2 |
| Silicone-treated titanium oxide (note 3) | 1.0 |
| Preservative | 0.1 |
| Fragrance | 0.1 |

(note 1): Long chain alkyl-containing acryl silicone resin: KP-561P (Product from Shin-Etsu Chemical Co., Ltd.)
(note 2): Methylphenyl polysiloxane: KF-54 (Product from Shin-Etsu Chemical Co., Ltd.)
(note 3): Treated with graft or copolymer of an acryl and a silicone: KP-541 (Product from Shin-Etsu Chemical Co., Ltd.)

The lipstick thus obtained exhibited glossy surface, light spreading properties, and refreshing feeling of use, without temporal change, oily or powdery feeling of use. The lipstick was also excellent in water resistance, water repellency, and cosmetic sustainability.

| Example 7: Eye liner | |
| --- | --- |
| (Components) | % by mass |
| Decamethyl cyclopentasiloxane | 22.0 |
| Dimethyl polysiloxane (6 mm$^2$/sec) | 5.0 |
| Black iron oxide | 20.0 |
| Vitamin E acetate | 0.2 |
| Jojoba oil | 2.0 |
| Bentonite | 3.0 |
| Polyoxyalkylene-modified organopolysiloxane of Preparation Example 2 | 2.0 |
| Ethanol | 10.0 |
| 1,3-butylene glycol | 10.0 |
| Preservative | 0.1 |
| Fragrance | 0.1 |
| Purified water | Remainder |

The eye liner thus obtained exhibited light spreading properties on eye lines, refreshing use feeling, significantly excellent usability and stability, excellent water resistance, perspiration resistance, and cosmetic sustainability without stickiness, temperature or temporal change.

Example 8: Milky lotion

| (Components) | % by mass |
|---|---|
| Decamethyl cyclopentasiloxane | 15.0 |
| Methylphenyl polysiloxane | 5.0 |
| Squalene | 5.0 |
| Tetra-2-ethyl hexanoic acid pentaerythritol | 5.0 |
| Polyoxyalkylene-modified organopolysiloxane of Preparation Example 1 | 3.0 |
| Organopolysiloxane elastomer spherical powder (note 1) | 2.0 |
| Hydrophobized silica (note 2) | 0.5 |
| Magnesium ascorbate phosphate | 1.0 |
| Sodium chloride | 1.0 |
| Polyethylene glycol 11000 | 1.0 |
| Propylene glycol | 8.0 |
| Preservative | 0.1 |
| Fragrance | 0.1 |
| Purified water | Remainder |

(note 1): Organopolysiloxane elastomer spherical powder: KMP-590 (Product from Shin-Etsu Chemical Co., Ltd.)
(note 2): Hydrophobized silica: aerosil R972 (Product from Nippon Aerosil Co., Ltd.)

The milky lotion thus obtained exhibited light spreading properties, significantly favorable usability and stability without stickiness, or temperature or temporal change.

Example 9: O/W cream

| (Components) | % by mass |
|---|---|
| Crosslinking dimethyl polysiloxane (note 1) | 8.0 |
| Crosslinking methylphenyl polysiloxane (note 2) | 2.0 |
| Isotridecyl isononanoate | 5.0 |
| Dipropylene glycol | 7.0 |
| Glycerin | 5.0 |
| Methyl cellulose (2% aqueous solution) (note 3) | 7.0 |
| Polyacrylamide-based emulsifying agent (note 4) | 2.0 |
| Polyoxyalkylene-modified organopolysiloxane of Preparation Example 2 | 0.5 |
| Guanine | 1.0 |
| Preservative | 0.1 |
| Fragrance | 0.1 |
| Purified water | Remainder |

(note 1): Crosslinking dimethyl polysiloxane: KSG-16 (Product from Shin-Etsu Chemical Co., Ltd.)
(note 2): Crosslinking methylphenyl polysiloxane: KSG-18 (Product from Shin-Etsu Chemical Co., Ltd.)
(note 3): Methyl cellulose: Metolose SM-4000 (Product from Shin-Etsu Chemical Co., Ltd.)
(note 4): Polyacrylamide-based emulsifying agent: Sepigel 305 (Product from SEPIC Corporation)

The O/W cream thus obtained exhibited fine texture, light spreading properties and foam touch, and refreshing use feeling, significantly excellent cosmetic sustainability, and excellent cosmetic stability without stickiness or greasiness, temperature or temporal change.

Example 10: Powder foundation

| (Components) | % by mass |
|---|---|
| Vaseline | 2.5 |
| Squalane | 3.0 |
| Polyoxyalkylene-modified organopolysiloxane of Preparation Example 4 | 0.5 |
| Glyceryl trioctanoate | 2.0 |
| Silicone-treated mica (note 1) | 40.0 |
| Silicone-treated talc (note 1) | Remainder |

Example 10: Powder foundation -continued

| (Components) | % by mass |
|---|---|
| Silicone-treated titanium oxide (note 1) | 10.0 |
| Silicone-treated microparticle titanium oxide (note 1) | 5.0 |
| Silicone-treated barium sulfate (note 1) | 10.0 |
| Phenyl-modified hybrid silicone compound powder (note 2) | 2.0 |
| Silicone powder (note 3) | 2.5 |
| Preservative | 0.1 |
| Fragrance | 0.1 |

(note 1): Treated with graft or copolymer of an acryl and a silicone: KP-541 (Product from Shin-Etsu Chemical Co., Ltd.)
(note 2): Phenyl-modified hybrid silicone compound powder: KSP-300 (Product from Shin-Etsu Chemical Co., Ltd.)
(note 3): Silicone powder: KMP-590 (Product from Shin-Etsu Chemical Co., Ltd.)

The powder foundation thus obtained exhibited light spreading properties, favorable contact feeling and cosmetic sustainability, and glossy finish without stickiness.

Example 11: Sun-cut cream

| (Components) | % by mass |
|---|---|
| Decamethyl cyclopentasiloxane | 17.5 |
| Graft or copolymer of an acryl and a silicone (note 1) | 12.0 |
| Polyoxyalkylene-modified organopolysiloxane of Preparation Example 4 | 1.0 |
| Glyceryl triisooctanoate | 5.0 |
| Polyether crosslinking dimethyl polysiloxane (note 2) | 5.0 |
| Lipophilized zinc oxide | 20.0 |
| Sodium chloride | 0.5 |
| 1.3-butylene glycol | 2.0 |
| Preservative | 0.1 |
| Fragrance | 0.1 |
| Purified water | Remainder |

(note 1): Treated with graft or copolymer of an acryl and a silicone: KP-545 (Product from Shin-Etsu Chemical Co., Ltd.)
(note 2): Polyether crosslinking dimethyl polysiloxane: KSG-210 (Product from Shin-Etsu Chemical Co., Ltd.)

The sun-cut cream thus obtained exhibited light spreading properties and contact feeling, and favorable UV protective effect on the skin without stickiness or temporal change.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

What is claimed is:

1. A block type organopolysiloxane represented by the formula (1),

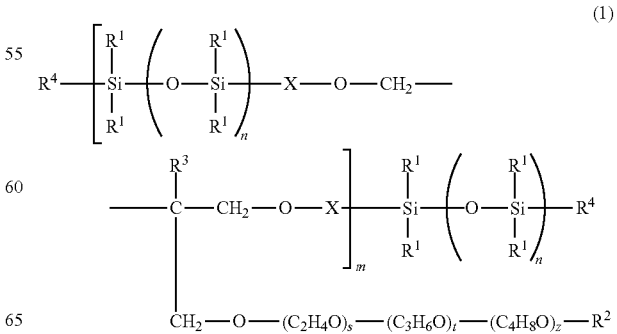

wherein each $R^1$ independently represents a monovalent hydrocarbon group having from 1 to 12 carbons; $R^2$ represents any of a hydrogen atom, a monovalent hydrocarbon group having 1 to 15 carbons, and a monovalent acyl group having 2 to 7 carbons; $R^3$ represents a hydrogen atom or a monovalent hydrocarbon group having 1 to 4 carbons; X represents a divalent hydrocarbon group having 2 to 15 carbons; n represents an integer of 1 or more; m represents an integer of 1 or more; s represents an integer of 0 to 100; t represents an integer of 0 to 50; z represents an integer of 0 to 50; s+t+z ≥1; and each $R^4$ independently represents a hydrogen atom, a hydroxyl group, an alkoxy group, or an organic group represented by the following general formula (2),

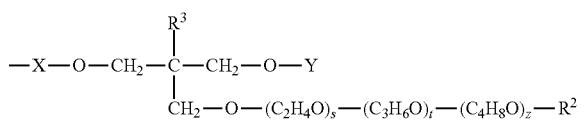

(2)

wherein Y represents a hydrogen atom, or a monovalent hydrocarbon group having 2 to 15 carbons and a carbon-carbon double bond.

2. The block type organopolysiloxane according to claim 1, wherein the block type organopolysiloxane is further represented by the formula (3),

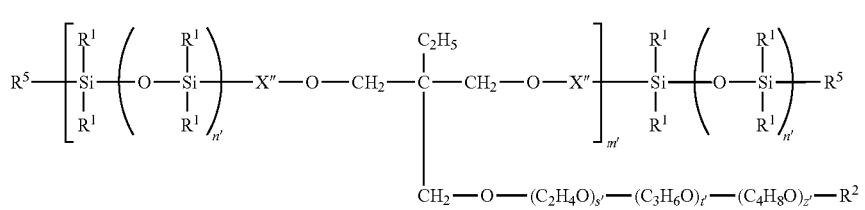

(3)

wherein each $R^1$ independently represents a monovalent hydrocarbon group having from 1 to 12 carbons; $R^2$ represents any of a hydrogen atom, a monovalent hydrocarbon group having 1 to 15 carbons, and a monovalent acyl group having 2 to 7 carbons; X" represents a —(CH$_2$)$_3$— or —CH$_2$CH(CH$_3$)CH$_2$—; n' represents an integer of 1 to 2000; m' represents an integer of 1 to 1000; s' represents an integer of 1 to 100; t' represents an integer of 0 to 50; z' represents an integer of 0 to 50; s'+t'+z'>1; and each $R^5$ independently represents a hydrogen atom, a hydroxyl group, an alkoxy group having 1 to 6 carbons, or an organic group represented by the following general formula (4),

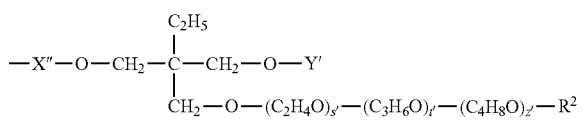

(4)

wherein Y' represents a hydrogen atom, —CH$_2$—CH═CH$_2$, —CH═CH—CH$_3$, —CH$_2$—C(CH$_3$)═CH$_2$, or —CH═C(CH$_3$)$_2$.

3. A cosmetic comprising the block type organopolysiloxane according to claim 1.

4. A cosmetic comprising the block type organopolysiloxane according to claim 2, 5. The cosmetic according to claim 3, wherein the cosmetic further contains any of water, a silicone oil, an ester oil, and a glyceride oil, or a mixture thereof and is in the form of emulsion.

6. The cosmetic according to claim 4, wherein the cosmetic further contains any of water, a silicone oil, an ester oil, and a glyceride oil, or a mixture thereof and is in the form of emulsion.

7. A method for producing the block type organopolysiloxane according to claim 1, wherein an organopolysiloxane represented by the following general formula (5) and a compound represented by the formula (6) are reacted in the presence of a transition metal catalyst,

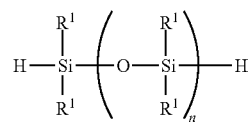

(5)

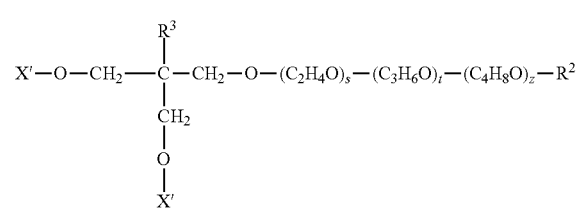

(6)

wherein $R^1$, $R^2$, $R^3$, n, s, t, and z are as defined in claim 1, and X' represents a monovalent hydrocarbon group having from 2 to 15 carbons and a carbon-carbon double bond on its one end.

8. A method for producing the block type organopolysiloxane according to claim 2, wherein an organopolysiloxane represented by the following general formula (5) and a compound represented by the formula (6) are reacted in the presence of at transition metal catalyst,

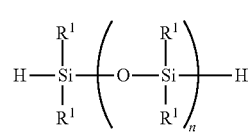

(5)

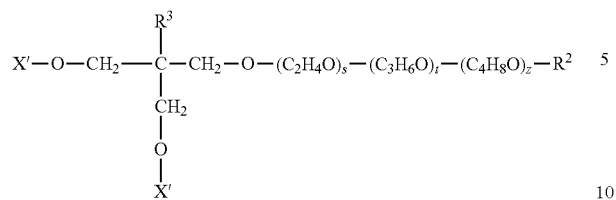 (6)

wherein $R^1$, $R^2$, $R^3$, n, s, t, and z are as defined in claim 2, and X' represents a monovalent hydrocarbon group having from 2 to 15 carbons and a carbon-carbon double bond on its one end.

9. The method for producing the block type organopolysiloxane according to claim 7, wherein a platinum or a rhodium is used as the transition metal catalyst.

10. The method for producing the block type organopolysiloxane according to claim 8, wherein a platinum or a rhodium is used as the transition metal catalyst.

* * * * *